US009052232B2

(12) United States Patent
Smith (10) Patent No.: US 9,052,232 B2
(45) Date of Patent: Jun. 9, 2015

(54) SPHEROID SAMPLE CELL FOR SPECTROMETER (71) Applicant: Malcolm C. Smith, Winchester, MA (US)

(72) Inventor: Malcolm C. Smith, Winchester, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 0 days.

(21) Appl. No.: 13/720,620

(22) Filed: Dec. 19, 2012

(65) Prior Publication Data

US 2014/0168649 A1  Jun. 19, 2014

(51) Int. Cl.
*G01J 3/02* (2006.01)
*G01J 3/42* (2006.01)
*G01N 21/03* (2006.01)

(52) U.S. Cl.
CPC ............... *G01J 3/0291* (2013.01); *G01J 3/42* (2013.01); *G01N 21/03* (2013.01)

(58) Field of Classification Search
CPC ...... G01J 3/0291; G01J 3/0272; G01J 3/0254
USPC ............... 356/236, 326, 246, 440, 437, 432; 250/336.1, 339.01, 339.05, 343
See application file for complete search history.

(56) References Cited

U.S. PATENT DOCUMENTS

| | | | |
|---|---|---|---|
| 3,704,951 A | 12/1972 | Chupp | |
| 3,815,977 A * | 6/1974 | Vasiliev et al. | 359/834 |
| RE33,213 E * | 5/1990 | Borden | 250/574 |
| 5,726,752 A * | 3/1998 | Uno et al. | 356/246 |
| 5,786,893 A * | 7/1998 | Fink et al. | 356/301 |
| 5,818,578 A * | 10/1998 | Inman et al. | 356/246 |
| 6,486,474 B1 * | 11/2002 | Owen et al. | 250/339.02 |
| 6,844,553 B2 * | 1/2005 | Daly et al. | 250/339.07 |
| 6,940,600 B1 * | 9/2005 | Smith | 356/437 |
| 7,215,428 B2 * | 5/2007 | McNeal et al. | 356/440 |
| 7,236,243 B2 * | 6/2007 | Beecroft et al. | 356/328 |
| 7,477,377 B2 | 1/2009 | Silver | |
| 7,876,443 B2 * | 1/2011 | Bernacki | 356/437 |
| 8,299,433 B2 * | 10/2012 | Majewski et al. | 250/338.1 |
| 2006/0072117 A1 * | 4/2006 | Ruth et al. | 356/453 |
| 2006/0268272 A1 * | 11/2006 | Liphardt et al. | 356/369 |
| 2008/0212216 A1 | 9/2008 | Milosevic et al. | |
| 2010/0079760 A1 * | 4/2010 | Bernacki | 356/437 |
| 2012/0261578 A1 * | 10/2012 | Scott et al. | 250/339.07 |

FOREIGN PATENT DOCUMENTS

WO    2008127648 A1    10/2008

OTHER PUBLICATIONS

Nishimoto et al., A compact, cylindrical multi-pass cell for sensitive detection of gas absorprtion, The Review of Laser Engineering, Supplemental vol. 2008, pp. 1276-1278.

(Continued)

*Primary Examiner* — Sang Nguyen
(74) *Attorney, Agent, or Firm* — Ion C. Abraham (57) ABSTRACT A sample cell for a spectrometer, and a spectrometer using such a sample cell. The sample cell may include a housing having a reflective inner surface which is at least a section of a spheroid bounding a cavity. A lens system receives electromagnetic radiation from a source and directs a converging beam through a port in the cavity to a focal point inside the cavity, such that the beam undergoes multiple reflections on the inner surface before exiting the cavity. Arrangements for adjusting beam cross-sectional area and angle are optionally provided. Methods which can be performed on such an apparatus and computer program products for performing such methods are further provided.

26 Claims, 3 Drawing Sheets

(56) References Cited

OTHER PUBLICATIONS

Tonomura et al., An experimental study on a cylindrical multi-pass cell, CLEO/Pacific Rim 2005. Pacific Rim Conference on Lasers and Electro-Optics, 2005., 1425-1426, (2005).

White, Long optical paths of large aperture, J.O.S.A., vol. 32, May 1942, pp. 285-288.
From Wikipedia, Multipass spectroscopic absorption cells, Dec. 18, 2012, 3 pages.

* cited by examiner

SPHEROID SAMPLE CELL FOR SPECTROMETER

FIELD

This invention generally relates to sample cells typically used in spectrometers, and spectrometers and methods using such sample cells.

BACKGROUND

Spectroscopy is an effective tool for identifying and characterizing a vast array of substances. Many spectroscopic techniques, instruments, and methods are well known. For example, in absorption spectroscopy a characteristic of a component in a sample, such as its presence or concentration, may be determined by evaluating an absorption characteristic of a light beam passing through a sample. The absorption characteristic is typically measured by generating a signal representing a comparison of the beam intensity as it enters and exits the sample, at one or more spectral regions of interest. It is well known that the entering and exiting intensities are typically related by Beer's law in which the ratio of exiting to entering intensity depends on the inverse of the exponent of the path length. That is, the greater the path length the greater the measured absorption signal, other factors remaining the same, up until a path length is reached where all light of the spectral region of interest is absorbed (the signal saturation point). After signal saturation no further change in absorption signal is possible even as the concentration of a species of interest in the sample increases. So it is useful to have longer path lengths to increase the absorption signal and thereby increase the signal to noise ratio from an instrument when the species of interest has a low concentration, but to allow for shorter path lengths to accommodate samples with higher concentrations of the species of interest without signal saturation.

Other forms of spectroscopy include Raman and fluorescence spectroscopy where a characteristic of a species of interest in response to a light beam are measured, but which characteristic is not simply an absorption characteristic of a light beam. For example, in Raman spectroscopy, light typically from a laser and of a known wavelength (typically infrared or near infrared) is directed at a specimen. The laser light (also sometimes referred to as the Raman pump) interacts with the electronic states in the molecules of the specimen and, as a result of this interaction, experiences selected wavelength shifting. The precise nature of this wavelength shifting depends upon the materials present in the specimen. A unique wavelength signature (typically called the Raman signature) is produced by each specimen. This unique Raman signature permits the specimen to be identified and characterized. While the absorption of the incident light beam is not measured directly, the measured signal in Raman spectroscopy also depends on the volume of sample observed which interacts with the incident beam. Thus, path length can also be important in Raman spectroscopy, fluorescence spectroscopy, and other forms of spectroscopy.

Spectrometers with very long sample cells can be conceived. However, very long sample cells can occupy too much space on a laboratory instrument and are particularly impractical on portable instruments. Herriott cells and White cells are well known as solutions to provide longer path lengths. In a Herriott cell, two mirrors face each other from opposite ends of an elongated cell and incident light enters through one mirror, and is reflected back and forth multiple times before exiting through one of the mirrors. A White cell uses three mirrors instead of two, and is able to accept high numerical aperture (NA) light. Such cells are still rectangular in shape and can be inconvenient in size, and are still of a fixed length.

SUMMARY

A spectrometer is provided which includes a housing having a reflective inner surface. This reflective inner surface comprises a section of a spheroid and bounding a cavity. An illumination unit directs a converging beam of electromagnetic radiation through a port in the housing to a focal point inside the cavity, such that the beam undergoes multiple reflections on the inner surface before exiting the cavity. A detector receives electromagnetic radiation which has exited the cavity.

The electromagnetic radiation in any embodiment may be light, though it will be appreciated that wherever "light" is referenced in any embodiment this could instead be replaced with "electromagnetic radiation".

Other embodiments of the invention may simply be a sample cell, which may be used as part of a spectrometer of the present invention. Such a sample cell may include a housing having a reflective inner surface which is at least a section of a spheroid bounding a cavity. A lens system receives light from a source and directs a converging light beam through a port in the cavity to a focal point inside the cavity, such that the beam undergoes multiple reflections on the inner surface before exiting the cavity.

The invention also provides methods which may be performed by any apparatus of the present invention, as well as computer program products which may perform such methods.

BRIEF DESCRIPTION OF THE DRAWINGS

Embodiments of the invention will now be described in which.

The same reference numerals are used in the different FIGS. to represent the same part. Drawings are not to scale unless otherwise stated.

DETAILED DESCRIPTION OF EMBODIMENTS OF THE INVENTION

Embodiments of the invention may have a reflective inner surface which is a section of different spheroids such as an oblate spheroid conceptually formed from the rotation of an ellipse, or a section of a sphere, such as an annular section taken through a plane which intersects the center of the sphere (and is typically symmetrical about that plane). Typically, embodiments of the present invention will have the illumination unit direct the converging light beam to a focal point inside the cavity such that an axis of the beam path does not intersect a center of the reflective surface. One advantage to using an inner surface that is spheroid but not exactly an annular section of a sphere symmetrical about a central plane, is that the inner surface can be shaped to at least partially or even completely correct any astigmatism in the light beam. That is, the curvature of the inner surface can differ in a "vertical direction" (that is, vertical to a plane of the reflected beam in the cavity) from the curvature in the "horizontal direction" (along the foregoing plane), in order to correct any such astigmatism. Astigmatism in this context references separation of focus in the horizontal and vertical directions, which could accumulate over many passes through the cell.

In any embodiment, the illumination unit changes an angle of the beam with respect to a normal to the reflective inner surface where the beam enters the cavity. This change allows for the number of passes of the light beam through the cell to be readily changed. Also, in any embodiment the illumination unit changes the cross-sectional area of the beam where the beam enters the cavity. This change in cross-sectional area of the entering beam can be used in conjunction with the foregoing feature changing the angle of the beam, or not used with that feature. Either the change in the angle of the entering beam, or the cross-sectional area of the entering beam, or both can be under control of a processor. The processor may change either of these, or both of these when both features are present, in response to a signal from the detector. For example, the signal may represent an intensity of light resulting from interaction of the light beam with a fluid inside the cavity, such as the absorption of some part of the beam spectrum by the fluid. The signal from the detector may either be directly from the detector or indirectly from the detector, for example after having been processed in any manner (such as evaluated by a processor for any characteristic such signal/noise ratio, or concentration of a gas component).

In any embodiment of the present invention the focal point of the entering beam could be mid-way between the at least one port at which the light beam enters the cavity and the reflective inner surface. Alternatively, this focal point could be less than or equal to 5%, 10% or 25% of the length of one pass of the beam within the cavity. By "pass of the beam" is referenced the path length of the beam between any two reflections (or any one reflection and the entry or exit port in the case where the beam is entering or exiting the cavity). Also, in any embodiment the illumination unit may be capable of varying the position of the focal point of the entering beam between the at least one port at which the beam enters the cavity and the reflective surface. As will be seen below, varying the entering angle of the beam may change the total number of beam passes through the cavity, while varying the cross-sectional area of the entering beam or the focal point varies the total cross-section of sample exposed to the light beam. Thus, all three techniques permit varying the signal from a sample in a spectral region of interest such that the signal/noise ratio can be adjusted by any or any combination of those three techniques.

Different illumination units may be used in any embodiment of the present invention. Typically, the illumination unit will include a light source and a lens system having one or more lenses to provide the focused beam of light from the source. For example, the illumination unit may provide a light beam which is not laser light, such as light from one or more light emitting diodes ("LED") or a polychromatic light source such as a filament or any black body source. Where the light is polychromatic, the illumination unit may include one or more achromatic lenses to focus the beam, although this is not required.

Any embodiment may be constructed such that the light beam enters and exits the cavity through a same port, that is the beam entry and exit ports are the same port (although the entering and exit beam may not overlap). While this provides a convenient construction, a separate beam entry and beam exit port may be used. Also, any embodiment may be arranged so that only a portion of the multiply reflected light beam exits the cavity on a first pass around the reflective inner surface. That is, where the light beam has traversed at least about 360 degrees around the cavity to an exit port, that port may partially reflect the light beam back into the cavity. For example, the beam exit port (which again may be the same as the beam entry port) may be partially reflective to light from inside the cavity. In this manner a portion of the beam may make multiple passes around the inside of the cavity before exiting the port, thereby effectively increasing the light beam path length through the cavity.

By using a very highly partially reflective surface at the beam exit port of any embodiment, it is possible to make the cavity a resonant cavity. For example, the reflective surface at the beam exit port may be at least 95%, or at least 99% reflective for a wavelength of light, with no more than 0.1%, 0.2%, 0.5% or 1% transmission of that wavelength of light. The principles of resonant cavities in spectrometry are well known and are described, for example, in U.S. Pat. No. 7,265,842 and U.S. Pat. No. 6,795,190 which are incorporated herein by reference. Resonant cavities provide very long beam path lengths at each of the resonant modes of the cavity. With a resonant cavity, a given resonant mode can be selected by changing the angle of the entering beam as previously described.

As previously mentioned, embodiments of the present invention may simply comprise a sample cell from the foregoing spectrometer. That is, the sample cell may just comprise the housing and reflective inner surface as previously described, and a lens system as previously described although the entire illumination unit may be included. Optionally, the lens system or illumination unit may be arranged to change either one or both the angle of the beam with respect to a normal to the reflective inner surface where the light beam enters the cavity, and cross-sectional area of the beam where it enters the cavity through the port, as previously described.

Any method of the present invention may include any of those features resulting from use of a spectrometer as described herein. For example, any method may include directing the converging light beam to a focal point inside a cavity bounded by a reflective inner surface which comprises an annular section of a sphere. Similarly, any such method may include varying any one or any combination of: the angle of the beam with respect to a normal to the reflective inner surface where the light beam enters the cavity; the cross-sectional area of the beam where the light beam enters the cavity; the focal point of the entering beam inside the cavity. Any of these may be varied in response to a signal from a processor. At least a portion of the light exiting the cavity may be detected at a detector, and may also be directed to a processor for analysis of one or more characteristics of the beam (such as absorption or signal/noise ratio).

Any computer program product of the present invention carries a computer program which, when loaded into a programmable processor, executes any method of the present invention. For example, the method may include directing a converging light beam to a focal point inside a cavity bounded by a reflective inner surface comprising a section of a spheroid, such that the beam undergoes multiple reflections on the inner surface before exiting the cavity. The method may also include receiving a signal from a detector resulting from light which has exited the cavity. Any such method may further include analyzing at least a portion of the light exiting the cavity for one or more characteristics (such as any one or more of: absorption by a sample in the cavity, emission of light from a sample in the cavity in response to the illuminating light, and signal/noise ratio).

Any embodiment of the present invention may be used for absorption spectroscopy (including Fourier Transform spectroscopy), and may also be used for other spectroscopy such as Raman spectroscopy or fluorescence spectroscopy. Raman spectroscopy may include Surface Enhanced Raman Spectroscopy ("SERS") where the reflective surface is reflective, and enhances the Raman signal in a manner known for SERS surfaces. Principles and different techniques of SERS spectroscopy is described, for example, in US20120287427, U.S. Pat. No. 8,241,922, U.S. Pat. No. 7,450,227, WO/2006/137885, and elsewhere. In any embodiment the sample of interest in the cavity may be a fluid, such as a gas or liquid.

By the reflective surface "bounding" the cavity is referenced that at least a part of the cavity's boundaries are defined by the inner surface. For example, when the inner surface is an annular section of a sphere which is open at the top and bottom (such as in FIGS. 1 and 2 below), the cavity is completely or substantially completely bounded by the inner surface. However, the cavity's boundaries can additionally be defined by other surfaces, such as when the cavity is enclosed by bottom and top surfaces over the foregoing annular section. "Identifying", "identifying the presence", "evaluating the presence", "analyze", or similar terms, includes either or both a qualitative evaluation (for example, the substance is or is not present) as well as a quantitative evaluate (that is, how much is present). "May" means optionally. For example, if any embodiment of the invention "may have feature X" then that embodiment can actually include feature X or not include feature X. "Or" in this application references that either one, or both. For example, if "A, B, or C" can be used, this means any one of them or any combination of two or more of them, can be used. A "processor" as used herein may be any hardware or hardware/software combination which is capable of carrying out the steps require of it. For example, a processor may be a suitably programmed microprocessor or application specific integrated circuit. For example, a processor could include a suitably programmed general purpose microprocessor, or an application specific integrated circuit ("ASIC"). In the case where the processor is programmable, it may not yet be programmed but only capable of being loaded with the program required so the processor can then accomplish the tasks required. "Light" reference any electromagnetic radiation in the wavelength range of 10 nanometers to 1 meter, and can includes ranges generally recognized as ultraviolet (10 to 400 nm), visible (400-700 nm), near infrared and infrared (700 nm-15 μm), and far infrared (15-1000 μm) and microwave (1 mm-1 m) ranges. By "path length" inside the cavity is referenced the length of a path the light takes from one feature to another, for example the path length of the beam from the entry port to its first reflection on the inner reflective surface, or the total path length of the beam from the entry to exit port. By an "axis" of the beam is referenced the center of the beam as viewed in a section across the beam area. When a range of any quantity is mentioned, that range specifically describes expressly includes every included whole unit value or next decimal place within that range (for example, at least 99% includes 99.0%, 99.1%, 99.2% and the like up to 100%). By a "width" of a beam is referenced the dimension of the beam at the reflective inner surface, along a plane in which the passes lie (sometimes referenced as a "horizontal" direction). By a "height" of the beam is referenced the dimension at the same location on the inner surface, but as measured in a direction perpendicular to the width (which direction is sometimes referenced as the "vertical" direction). It will be appreciated that any embodiment of the present invention may have features additional to those cited. Sometimes the term "at least" is used for emphasis in reference to a feature. However, it will be understood that even when "at least" is not used, additional numbers or type of the referenced feature may still be present. All references cited in the present application are fully incorporated herein by reference. However, where anything in any incorporated reference contradicts anything stated in the present application, the present application prevails. The order of any sequence of events in any method recited in the present application, is not limited to the order recited. Instead, the events may occur in any order, including simultaneously, which is logically possible. Any spectrometer of the present invention may be hand-held. By "hand-held" in this context is referenced a spectrometer instrument which weighs less than 10 kg, and more typically less than 5, 2, 1, or even less than 0.5 or 0.2 kg, and may have dimensions of less than 50 cm or 30 cm in each dimension, and one of the dimensions (the thickness) may even be less than 10 cm or 5 or 3 cm. A "hand-held" spectrometer will often be battery powered with the battery typically fitting within the foregoing dimensions and included in the foregoing weights, although a separate power supply could be provided and connected to the spectrometer (for example, through a USB or other cable).

Figure 1:
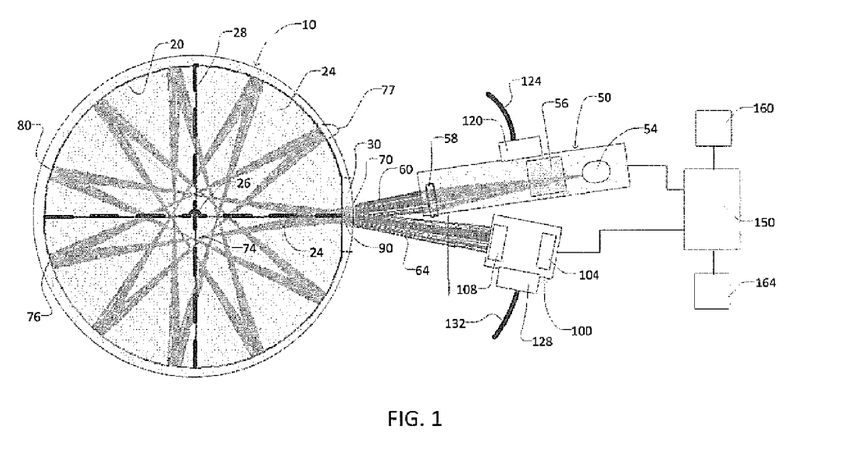
FIG. 1 illustrates a top view of a spectrometer of an embodiment of the present invention which uses a sample cell of an embodiment of the present invention. The embodiment is shown in use with 11 passes of the incident beam through the sample cell. The plane on which those passes lie is sometimes referenced as a horizontal direction herein.
Figure 2:
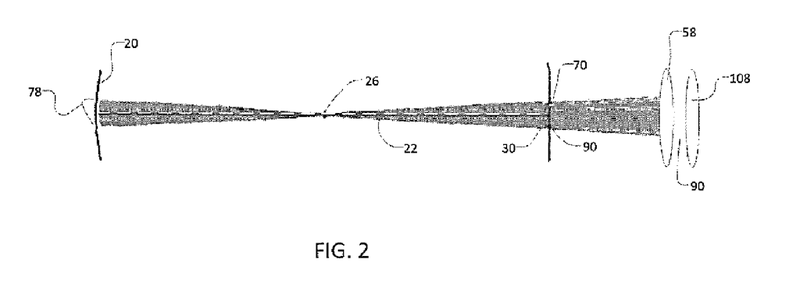
FIG. 2 illustrates a vertical cross-section through part of the spectrometer of FIG. 1.

Turning to the embodiment shown in FIG. 1, the spectrometer has a sample cell defined by housing 10. Housing 10 has a reflective inner surface 20, such as a mirror for light, which may be of any suitable material having at least 90%, at least 95%, or greater reflectivity for all wavelengths of interest over which the spectrometer is to operate. Inner surface 20 defines a cavity 24 therein, into which a sample for testing can be received. As can be seen from FIGS. 1 and 2, inner surface 20 is an annular section taken symmetrically about the center of a spheroid and has a center 26 through which two orthogonal axes 24, 28 pass. Cavity 24 is open on a top and bottom, as seen in FIG. 2. This is convenient where the sample is ambient atmosphere such as when the spectrometer is in a portable instrument worn by a user to sample ambient atmosphere. However, it will be appreciated that cavity 24 can be closed and port 30 can be an optically transparent port, and controlled access permitted for samples to be admitted to cavity 24 from specific locations (for example, gasses from a smokestack or for analyzing swab contents where a swab is heated to drive off volatile components to be measured by the cell). Housing 10 also includes a port 30 which acts both as an entry and exit port for a light beam, as will be described. An illumination unit 50 includes a polychromatic light source 54, a selector 56 which can select different spectral ranges of light from source and direct those to lens system 58. For example, selector 56 may be a diffraction grating and slit which are arranged and operated in a known manner, or may be an interferometer in the case of a Fourier Transform spectrometer.

Lens system 58 may include one or more lenses to direct an entering beam of light 60 through port 30 at an angle to axis 25 such that it converges at a focal point 74 mid-way along beam 60 between port 30 and a position 76 where it first reflects from inner surface 20. Note that an axis of the beam does not intersect center 26 of inner surface 20. Beam 60 has a width 77, and height 78, at the position of each reflection on inner surface 20. With the foregoing arrangement it will be seen that beam 60 will undergo multiple reflections at inner surface 20 before exiting cavity 24 at position 90 as exiting beam 64. Lens system 58 is capable of varying the cross-sectional area of beam 60 as measured at position 70 where it enters cavity 24 through port 30. Where the beam 60 is relatively narrow, as illustrated in FIG. 2, then lens system 58 may vary this cross-section by only varying the width of the beam. However, it will be appreciated that lens system may also vary this cross-section by adjusting beam thickness or diameter, particularly where inner surface 20 represents a thicker annular section of a sphere. The width 77 is the same at each reflection, while the height 78 at each reflection is also the same. However, the width 77 and height 78 may not be the same as each other. This is particularly true where one wishes to obtain the maximum number of passes of the beam in the cavity. In this situation the beam 60 may have a height 78 which is greater than the width 77 to avoid overlap of different beam passes at the inner surface 20 and resulting premature exit of some light from the cavity. Such beam shaping can be accomplished by providing illumination unit 50 with an appropriate shaped arperture or a more complex lens system 58.

Lens system 58 is also capable of varying the position of focal point 74 between positions 70 and 76, so that focal point 74 may be near axis 74 as shown in FIG. 1, or may be elsewhere between positions 70 and 76. Exiting beam 64 passes to a detector unit 100 which includes a second lens system 108 of one or more lenses to direct beam 64 onto a detector 104 which converts received light intensity to a signal. Intensity of light from source 54, wavelength region selection by selector 56, and focal point and cross-sectional area of beam 60, can all be under control of a processor 150 which also receives the signal from detector 104.

The spectrometer of FIG. 1 also includes a first angle adjust unit 120 which moves illumination unit back and forth along curved track 124, and a second angle adjust unit 128 which moves detector unit 100 back and forth along curved track 128. Both angle adjust units 120 and 128 are controlled by processor 150 such that movement will typically be in opposite directions. For example, if illumination unit 50 is moved in a counter-clockwise direction so as to increase the angle between beam 60 and axis 24, then detector unit 100 would be moved in a clockwise direction an equal (but opposite) angular distance. This ensures that detector 100 will be in position to receive beam 64 even as the angle of beam 60 with respect to axis 24 is varied. Processor 150 may also perform an analysis of any signal received from detector 104 (such as determining absorption of beam 60 by a sample within cavity 24, or evaluating signal/noise ratio), and save that analysis and/or raw signal data to a memory 160.

Figure 3:
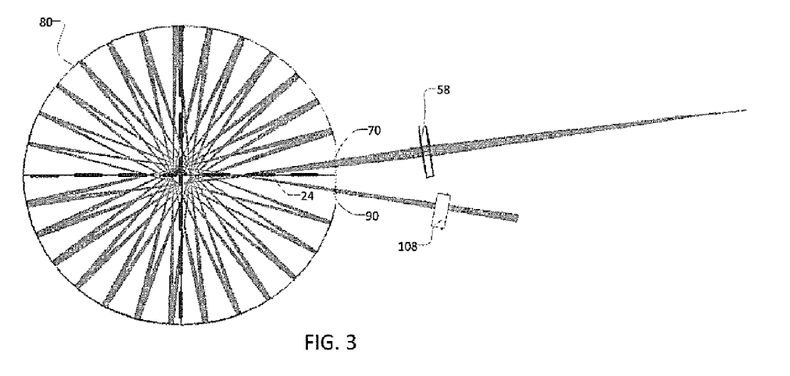
FIG. 3 is a view similar showing some of the components of the spectrometer of FIG. 1, but illustrating use of an incident beam of relatively low cross-sectional area with 27 passes through the sample cell.
Figure 4:
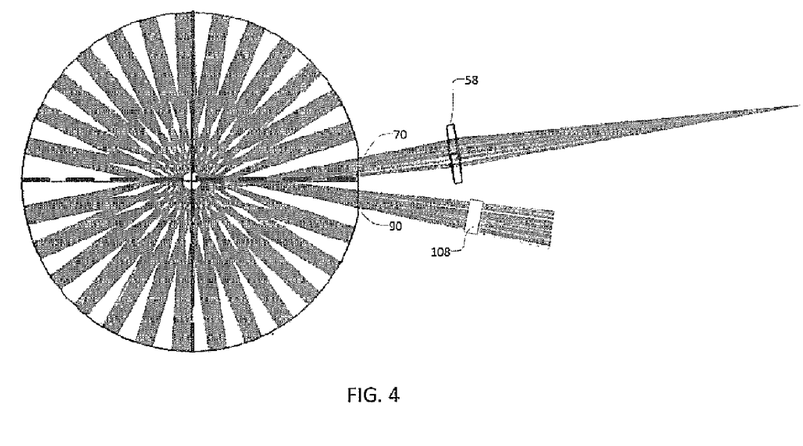
FIG. 4 is a view similar to FIG. 3 but showing an incident beam of relatively high cross-sectional area and with 27 passes through the sample cell.

It will be appreciated that by varying the angle of beam 60 with respect to axis 24 the total number of passes of the beam through cavity, and hence the total path length of the beam within cavity 24, can be varied. Similarly, adjusting lens system 58 can vary the cross-section area of beam 60 as it enters cavity 24 at position 70. By varying either or both of these, the total cross-sectional area to which a sample in cavity is exposed to incoming light, can be varied. For example, FIG. 1 shows 11 passes of the incoming beam through cavity 24 between exiting and entering port 30. On the other hand, by decreasing the angle between beam 60 and axis 24, the number of passes can be increased to 27 passes as illustrated in FIG. 3. Similarly, by adjusting lens system 58 the cross-sectional area of the light beam can be varied as shown in FIG. 4. Additionally, the intensity of light source 54 can also be varied. Any of the foregoing can be varied under control of processor 150. This variation may be in response to an operator identifying a change in sample type or some other condition, through operator input device 164, or in response to a measured characteristic of the signal from detector 104. For example, processor 150 may determine that a signal from detector 104 represents a signal with a signal/noise ratio that is unacceptably low. In response, processor 150 may do any one or more of the following: increase the intensity from light source 54; change the cross-sectional area of beam 60, change the focal point of beam 60; change the number of passes of the beam through cavity 24 by using angle adjust units 120, 128 to adjust the angle of beam 60 with respect to axis 24. Additionally, processor 150 may alter the wavelength region selected by selector particularly where none of the foregoing changes have succeeded in providing a signal with a required characteristic. For example, where changing light intensity, cross-sectional area, and number of passes, does not result in a signal with a required characteristic (such as a minimum signal/noise ratio), this may mean that another wavelength region of interest has to be selected to measure the required sample characteristic (such as concentration of a gas).

It will be appreciated that the spectrometer can be constructed with a cavity 24 of various dimensions, depending upon desired application. For example, a 2 meter total path length may be obtained with a circular cross section disk-shaped cavity 75 mm in diameter and 6 mm thick. This form factor is especially for a hand-held Fourier Transform Infra-Red ("FTIR") optical engine. A spectrometer with such a cavity may have adequate sensitivity to detect the concentration of many different gasses of interest down to several hundred parts per million, or even 100 parts per million, or better.

Figure 5:
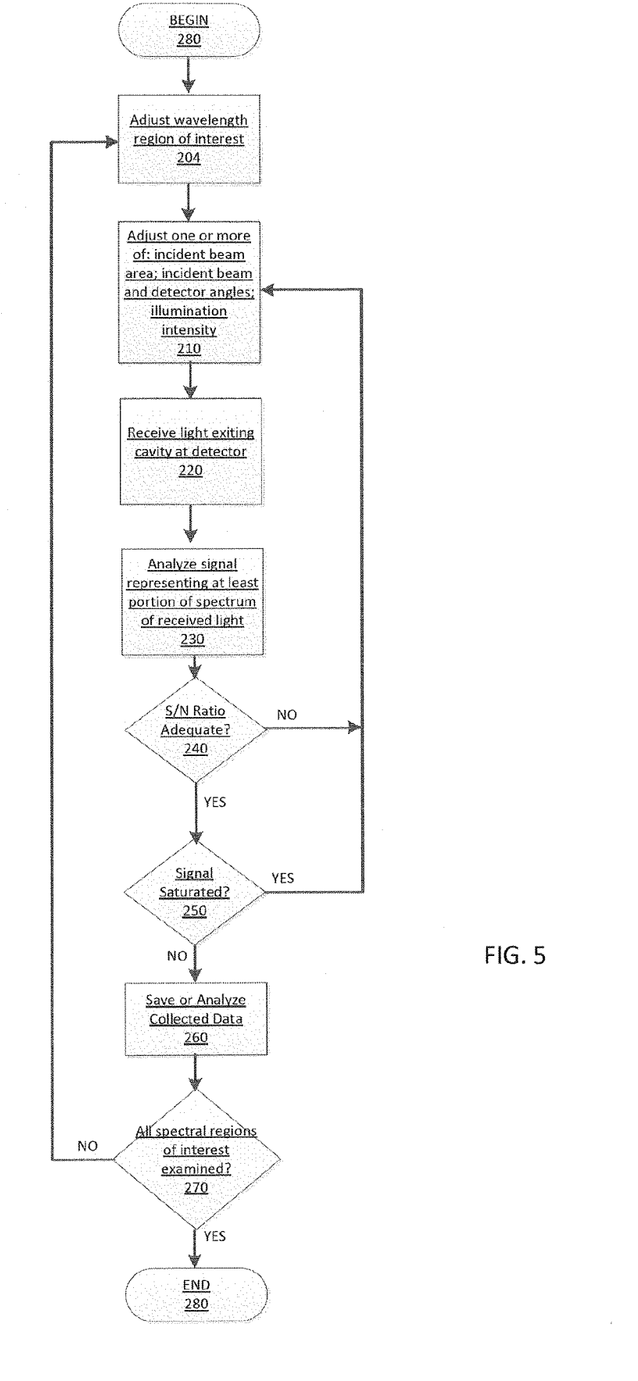
FIG. 5 is a flowchart illustrating a method of the present invention.

Turning now to FIG. 5, a method of operation of the spectrometer of FIGS. 1-4 will be illustrated. It will be assumed that the sample of interest (for example, ambient air) is present in cavity 24. The routine illustrated begins (280) with a command (such as input by an operator) to test a sample. An initial wavelength region of interest is selected (204) by adjusting selector 56 accordingly. This selection may be based on the type of sample, or may just be an initial region of a larger region to be scanned sequentially (for example, 400-405 nm when the visible range is to be scanned in 5 nm increments). The beam area of beam 60 (sometimes referenced as the "incident beam"), incident beam and detector unit angles, and illumination intensity, are all adjusted (210) as needed. Again, these adjustments may simply be some standard initial setting or may be based on the sample type, for example. Light exiting cavity 24 is received (220) at detector 104 and the resulting signal analyzed (230) by processor 150. A desired characteristic (such as signal/noise ratio) is evaluated (240) by processor 240 to see if it meets a requirement (such as a minimum acceptable value). If the desired characteristic does not meet the requirement, processor 150 may then again adjust (210) any of the features described until the characteristic is met. If the requirement is not met, the wavelength region of interest may be changed (204) by processor 150, or an error message generated (not shown). If the requirement is met, processor 150 may also check (250) if the signal is saturated. If the signal is saturated processor 150 may again adjust (210) any of those features until both the requirement is met with a signal that is not saturated. If this is not possible, processor 150 may again change (204) the wavelength region of interest and repeat the foregoing sequence. If the requirement is still not met without a saturated signal, processor 150 may then generate an error message (not shown). If the requirement is met with a signal that is not saturated, processor 150 may then analyze the collected data as desired and/or save the analysis results and/ or the raw data in memory (260). Processor then changes the spectral region selected by selector 56 until all desired spectral regions of interest have been examined (270), at which point the process ends (280) until another analysis is to be performed.

Particular embodiments of the present invention have been described in detail above. However, it will be apparent that variations and modifications of the described embodiments are possible. In one such variation, the incident light beam need not make a complete 360 degree pass around cavity 24. For example, a separate exit port could be provided so the beam could exit cavity 24 at position 80 or inner surface could be constructed so that the incident beam completes only about 180 or 270 degrees after multiple reflections. However, this would not make full use of the volume of cavity 24. Similarly, inner surface 20 may not be reflective around its entire surface it only being reflective at positions where the beam actually reflects from it. However, such a construction may be more difficult to make than simply making all of inner surface 20 (except port 30) reflective and will also limit the variation in beam diameter of incident beam that can be used. Also, port 30 could be closed by means of a surface which is partially reflective (for example, at least 99% reflective) particularly where a resonant cavity was desired.

The invention claimed is:

1. A spectrometer, comprising:
    a housing having a reflective inner surface comprising a section of a spheroid bounding a cavity;
    an illumination unit which directs a converging non-laser light polychromatic light beam, the converging non-laser light polychromatic light beam having a cross-sectional area vertical to a plane of the converging non-laser light polychromatic light beam in the cavity, through a port in the housing to a focal point inside the cavity mid-way between the reflective inner surface and the port in the housing where the light beam enters the cavity, such that the beam undergoes multiple reflections on the inner surface before exiting the cavity, the illumination unit further adapted to vary the vertical cross-sectional area of the beam at the port in the housing where the beam enters the cavity; and
    a detector to receive light which has exited the cavity.

2. A spectrometer according to claim 1 wherein the section of a spheroid is an annular section of a sphere.

3. A spectrometer according to claim 2, wherein the illumination unit directs the converging light beam to a focal point inside the cavity such that an axis of the beam does not intersect a center of the reflective surface.

4. A spectrometer according to claim 3 wherein the illumination unit varies an angle of the beam with respect to a normal to the reflective inner surface where the beam enters the cavity.

5. A spectrometer according to claim 4, additionally comprising a processor which varies each of the angle of the beam and the vertical cross-sectional area of the beam in response to a signal from the detector.

6. A spectrometer according to claim 4 wherein the processor varies each of the angle of the beam and the vertical cross-sectional area of the beam in response to a signal from the detector which signal represents an intensity of light resulting from interaction of the light beam with a fluid inside the cavity.

7. A spectrometer according to claim 2 wherein the focal point is mid-way between the reflective inner surface and the port in the housing where the light beam enters the cavity.

8. A spectrometer according to claim 1 wherein the illumination unit comprises a polychromatic light source and an achromatic lens system.

9. A spectrometer according to claim 1 wherein the light beam enters and exits the cavity through a same port.

10. A spectrometer according to claim 1 wherein only a portion of the multiply reflected light beam exits the cavity on a first pass around the reflective inner surface.

11. A spectrometer according to claim 10 wherein the light beam exits the cavity through a port which partially reflects the light beam back into the cavity.

12. A spectrometer according to claim 10 wherein the cavity is a resonant cavity.

13. A spectrometer according to claim 1 wherein the inner surface has a curvature in a horizontal direction which is different from the curvature in a vertical direction, so as to at least partially correct any astigmatism in the beam.

14. A spectrometer according to claim 1 wherein the width of the beam at the inner surface is less than the height of the beam at the same location.

15. A spectrometer according to claim 1 configured as a hand-held spectrometer.

16. A sample cell for a spectrometer, comprising:
    a housing having a reflective inner surface which is at least a section of a spheroid defining a cavity;
    a lens system to receive light from a source and direct a converging non-laser light polychromatic light beam, the converging non-laser light polychromatic light beam having a cross-sectional area vertical to a plane of the converging non-laser light polychromatic light beam in the cavity, through a port in the cavity to a focal point inside the cavity, such that the beam undergoes multiple reflections on the inner surface before exiting the cavity, the lens system further configured to vary the vertical cross-sectional area of the beam where the beam passes through the port.

17. A sample cell according to claim 16 wherein the lens system varies an angle of the beam with respect to a normal to the reflective inner surface where the light beam enters the cavity.

18. A sample cell according to claim 16 wherein the section of a spheroid is an annular section of a sphere.

19. A sample cell according to claim 16 configured to be disposed within a hand-held spectrometer.

20. A method comprising:
    directing a converging non-laser light polychromatic light beam through a port in a cavity to a focal point inside the cavity defined by a reflective inner surface comprising a section of a spheroid, the converging non-laser light polychromatic light beam having a cross-sectional area vertical to a plane of the converging non-laser light polychromatic light beam in the cavity, such that the beam undergoes multiple reflections on the inner surface before exiting the cavity;
    varying the vertical cross-sectional area of the beam where the beam passes through the port; and,
    receiving at a detector light which has exited the cavity.

21. A method according to claim 20 wherein the converging light beam is directed to a focal point inside a cavity bounded by a reflective inner surface which comprises an annular section of a sphere.

22. A method according to claim 21 additionally comprising varying the angle of the beam with respect to a normal to the reflective inner surface where the light beam enters the cavity.

23. A method according to claim 21 wherein the varying is in response to a signal from a processor.

24. A computer program product carrying a non-transitory computer program which, when loaded into a programmable processor, executes the method of:
- directing a converging non-laser light polychromatic light beam through a port in a cavity to a focal point inside the cavity bounded by a reflective inner surface comprising a section of a spheroid, the converging non-laser light polychromatic light beam having a cross-sectional area vertical to a plane of the converging non-laser light polychromatic light beam in the cavity, such that the beam undergoes multiple reflections on the inner surface before exiting the cavity;
- varying the vertical cross-sectional area of the beam where the beam passes through the port; and,
- receiving a signal from a detector resulting from light which has exited the cavity.

25. A computer program product according to claim 24 wherein the executed method additionally comprises:
- varying the angle of the beam with respect to a normal to the reflective inner surface where the light beam enters the cavity.

26. A method according to claim 20 further comprising:
- selecting a hand-held spectrometer to perform the directing, varying and receiving.

* * * * *